United States Patent
Fauber et al.

(10) Patent No.: US 11,223,543 B1
(45) Date of Patent: Jan. 11, 2022

(54) RECONSTRUCTING TIME SERIES DATASETS WITH MISSING VALUES UTILIZING MACHINE LEARNING

(71) Applicant: Dell Products L.P., Round Rock, TX (US)

(72) Inventors: Benjamin Fauber, Austin, TX (US); Ashutosh Singh, Austin, TX (US)

(73) Assignee: Dell Products L.P., Round Rock, TX (US)

( * ) Notice: Subject to any disclaimer, the term of this patent is extended or adjusted under 35 U.S.C. 154(b) by 0 days.

(21) Appl. No.: 17/035,976

(22) Filed: Sep. 29, 2020

(51) Int. Cl.
| | |
|---|---|
| G06N 20/00 | (2019.01) |
| H04L 12/26 | (2006.01) |
| G06N 3/04 | (2006.01) |
| H04L 12/24 | (2006.01) |
| G06K 9/62 | (2006.01) |
| G06N 3/063 | (2006.01) |

(52) U.S. Cl.
CPC .......... *H04L 43/067* (2013.01); *G06K 9/6298* (2013.01); *G06N 3/04* (2013.01); *G06N 3/063* (2013.01); *H04L 41/0813* (2013.01); *H04L 43/08* (2013.01)

(58) Field of Classification Search
None
See application file for complete search history.

(56) References Cited

U.S. PATENT DOCUMENTS

| | | | | |
|---|---|---|---|---|
| 9,600,540 | B1 * | 3/2017 | Bruno | G06F 16/285 |
| 2017/0220938 | A1 * | 8/2017 | Sainani | G06F 16/2428 |
| 2020/0093386 | A1 * | 3/2020 | Biswas | A61B 5/681 |
| 2020/0342362 | A1 * | 10/2020 | Soni | G06N 3/0472 |
| 2021/0096203 | A1 * | 4/2021 | Fernandez Villena | G01R 33/56581 |

(Continued)

FOREIGN PATENT DOCUMENTS

WO PCTUS2021029565 10/2021

OTHER PUBLICATIONS

D. Bertsimas et al., "From Predictive Methods to Missing Data Imputation: An Optimization Approach," Journal of Machine Learning Research, vol. 18, 2018, pp. 1-39.

(Continued)

*Primary Examiner* — James A Edwards
(74) *Attorney, Agent, or Firm* — Ryan, Mason & Lewis, LLP (57) ABSTRACT

An apparatus comprises a processing device configured to obtain a time series dataset having missing values, the time series dataset comprising monitoring data associated with one or more assets. The processing device is also configured to generate, utilizing a machine learning algorithm, a reconstructed time series dataset having imputed values for the missing values in the obtained time series dataset, the machine learning algorithm comprising a generative network implementing inverse network parameter determination for network parameters of the generative network. The processing device is further configured to classify patterns in the obtained time series dataset utilizing the reconstructed time series dataset, to select remedial actions for controlling at least one of the one or more assets based at least in part on the classified patterns in the obtained time series dataset, and to initiate the selected remedial actions to control the at least one asset.

20 Claims, 7 Drawing Sheets

(56) References Cited

U.S. PATENT DOCUMENTS

2021/0113098 A1* 4/2021 Yamada ............... G06N 20/00

OTHER PUBLICATIONS

C. M. Bishop, "Pattern Recognition and Machine Learning," Information Science and Statistics. Springer, New York, 2006, 758 pages.
W. Cao et al., "BRITS: Bidirectional Recurrent Imputation for Time Series," 32nd Conference on Neural Information Processing Systems, Montreal, Canada, 2018, 11 pages.
P. Chakrabarty et al., "The Spectral Bias of the Deep Image Prior," arXiv:1912.08905v1, Dec. 18, 2019, 7 pages.
Z. Che et al., "Recurrent Neural Networks for Multivariate Time Series with Missing Values," arXiv:1606.01865v2, Nov. 7, 2016, 14 pages.
A. Dosovitskiy et al., "Inverting Visual Representations with Convolutional Networks," arXiv:1506.02753v4, Apr. 26, 2016, 15 pages.
A. Graves, "Generating Sequences with Recurrent Neural Networks," arXiv:1308.0850v5, Jun. 5, 2014, 43 pages.
H. Greiner, "A Survey on Univariate Data Interpolation and Approximation by Splines of Given Shape," Mathematical and Computer Modelling, vol. 15, No. 10, 1991, pp. 97-106.
R. Heckel et al., "Deep Decoder: Concise Image Representations from Untrained Non-convolutional Networks," arXiv:1810.03982v2, Feb. 22, 2019, 17 pages.
S. Ioffe et al., "Batch Normalization: Accelerating Deep Network Training by Reducing Internal Covariate Shift," arXiv:1502.03167v3, Mar. 2, 2015, 11 pages.
Y. Lecun et al., "Deep Learning," Nature, vol. 521, May 28, 2015, pp. 436-444.
C. Ledig et al., "Photo-Realistic Single Image Super-Resolution Using a Generative Adversarial Network," arXiv:1609.04802v5, May 25, 2017, 19 pages.
J. Liu et al., "Image Restoration using Total Variation Regularized Deep Image Prior," arXiv:1810.12864v1, Oct. 30, 2018, 8 pages.
Y. Luo et al., "Multivariate Time Series Imputation with Generative Adversarial Networks," 32nd Conference on Neural Information Processing Systems, Montreal, Canada, 2018, 12 pages.
A. Mahendran et al., "Understanding Deep Image Representations by Inverting Them," arXiv:1412.0035v1, Nov. 26, 2014, 9 pages.
W. McKinney, "Python for Data Analysis," O'Reilly Media, Inc., 1st edition, 2012, 470 pages.
S. Moritz et al., "Comparison of Different Methods for Univariate Time Series Imputation in R," Cologne University of Applied Sciences, Oct. 2015, 20 pages.
F. Radenovic et al., "Fine-tuning CNN Image Retrieval with No Human Annotation," arXiv:1711.02512v2, Jul. 10, 2018, 14 pages.
S. Ravula et al., "One-dimensional Deep Image Prior for Time Series Inverse Problems," arXiv:1904.08594v1, Apr. 18, 2019, 20 pages.
R. Tibshirani, "Regression Shrinkage and Selection via the Lasso: A Retrospective," Journal of the Royal Statistical Society, vol. B, No. 73, 2011, pp. 273-282.
D. Ulyanov et al., "Deep Image Prior," In Proceedings of the IEEE Conference on Computer Vision, 2018, pp. 9446-9454.
Z. Guo et al., "A Data Imputation Method for Multivariate Time Series Based on Generative Adversarial Network." Neurocomputing, vol. 360, 2019, pp. 185-197.
G. Hawthorne et al., "Imputing Cross-Sectional Missing Data: Comparison of Common Techniques." Australian and New Zealand Journal of Psychiatry, vol. 39, No. 7, 2005 pp. 583-590.
H. Junninen et al., "Methods for Imputation of Missing Values in Air Quality Data Sets." Atmospheric Environment, vol. 38, No. 18, 2004, pp. 2895-2907.
D. M. Kreindler et al., "The Effects of the Irregular Sample and Missing Data in Time Series Analysis." Nonlinear Dynamical Systems Analysis, 2016, pp. 135-157.
F. Schmidt et al., "IFTM—Unsupervised Anomaly Detection for Virtualized Network Function Services," IEEE International Conference on Web Services (ICWS), Jul. 2, 2018, pp. 187-194.
Y. Yuxuan et al., "Learning-Based Real-Time Event Identification Using Rich Real PMU Data," Cornell University Library, arxiv.org, Jun. 17, 2020, 8 pages.
S. Jeong et al., "Sensor Data Reconstruction Using Bidirectional Recurrent Neural Network with Application to Bridge Monitoring," Advanced Engineering Informatics, Oct. 1, 2019, 14 pages, vol. 42.
H. Khorasgani et al., "A Methodology for Monitoring Smart Buildings with Incomplete Models," Applied Soft Computing, Jun. 28, 2018, pp. 396-406, vol. 71.

* cited by examiner

RECONSTRUCTING TIME SERIES DATASETS WITH MISSING VALUES UTILIZING MACHINE LEARNING

FIELD

The field relates generally to information processing, and more particularly to techniques for managing data.

BACKGROUND

Time series data is produced in many information processing systems. For example, computing devices in an information technology infrastructure may be a source of telemetry data that comprises time series datasets. When such telemetry data is produced, there may be missing values as a result of failure to measure, incomplete data capture, accidental or intentional deletion of data, etc. There is a need for imputing missing values with reasonable values to enable various analysis to be performed on the telemetry data. For example, some analysis techniques utilize machine learning algorithms that rely on having complete datasets available.

SUMMARY

Illustrative embodiments of the present disclosure provide techniques for reconstructing time series datasets with missing values utilizing machine learning.

In one embodiment, an apparatus comprises at least one processing device comprising a processor coupled to a memory. The at least one processing device is configured to perform the step of obtaining a time series dataset having one or more missing values, the time series dataset comprising monitoring data associated with one or more assets. The at least one processing device is also configured to perform the step of generating, utilizing a machine learning algorithm, a reconstructed time series dataset having one or more imputed values for the one or more missing values in the obtained time series dataset, the machine learning algorithm comprising a generative network implementing inverse network parameter determination for network parameters of the generative network. The at least one processing device is further configured to perform the steps of classifying one or more patterns in the obtained time series dataset utilizing the reconstructed time series dataset, selecting one or more remedial actions for controlling at least one of the one or more assets based at least in part on the classified one or more patterns in the obtained time series dataset, and initiating the selected one or more remedial actions to control the at least one asset.

These and other illustrative embodiments include, without limitation, methods, apparatus, networks, systems and processor-readable storage media.

DETAILED DESCRIPTION

Illustrative embodiments will be described herein with reference to exemplary information processing systems and associated computers, servers, storage devices and other processing devices. It is to be appreciated, however, that embodiments are not restricted to use with the particular illustrative system and device configurations shown. Accordingly, the term "information processing system" as used herein is intended to be broadly construed, so as to encompass, for example, processing systems comprising cloud computing and storage systems, as well as other types of processing systems comprising various combinations of physical and virtual processing resources. An information processing system may therefore comprise, for example, at least one data center or other type of cloud-based system that includes one or more clouds hosting tenants that access cloud resources.

Figure 1:
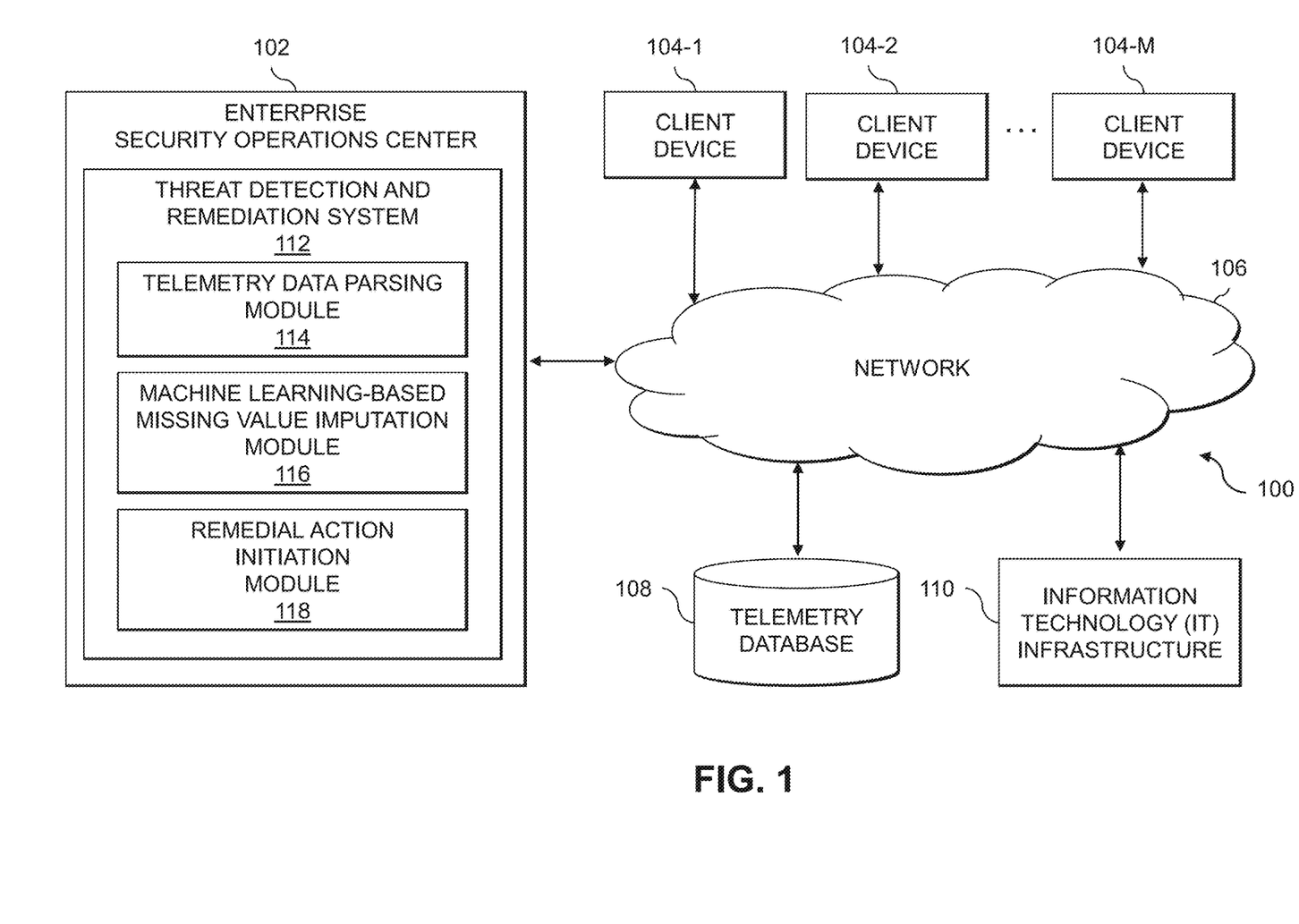
FIG. 1 is a block diagram of an information processing system for reconstructing time series datasets with missing values utilizing machine learning in an illustrative embodiment.

FIG. 1 shows an information processing system 100 configured in accordance with an illustrative embodiment. The information processing system 100 is assumed to be built on at least one processing platform and provides functionality for reconstructing time series datasets with missing values utilizing machine learning. The information processing system 100 includes an enterprise security operations center (SOC) 102, which is coupled via a network 106 to an information technology (IT) infrastructure 110. The IT infrastructure 110, or assets thereof, are assumed to be accessed over the network 106 by client devices 104-1, 104-2, . . . 104-M (collectively, client devices 104). The assets of the IT infrastructure may include, by way of example, physical and virtual computing resources in the enterprise system 110. Physical computing resources may include physical hardware such as servers, storage systems, networking equipment, Internet of Things (IoT) devices, health monitoring devices or other types of wearable devices, satellite devices, other types of processing and computing devices, etc. Virtual computing resources may include virtual machines (VMs), software containers (also referred to herein as containers), etc. The assets of the IT infrastructure 110 are assumed to produce time series data (e.g., telemetry data) that is stored in the telemetry database 108 as described in further detail below.

The client devices 104 may comprise, for example, physical computing devices such as IoT devices, mobile telephones, laptop computers, tablet computers, desktop computers or other types of devices utilized by members of an enterprise, in any combination. Such devices are examples of what are more generally referred to herein as "processing devices." Some of these processing devices are also generally referred to herein as "computers." The client devices 104 may also or alternately comprise virtualized computing resources, such as VMs, containers, etc.

The client devices 104 in some embodiments comprise respective computers associated with a particular company, organization or other enterprise. At least portions of the system 100 may thus be referred to herein as collectively comprising an "enterprise." Numerous other operating scenarios involving a wide variety of different types and arrangements of processing nodes are possible, as will be appreciated by those skilled in the art. In some embodiments, the IT infrastructure 110 is associated with an enterprise system. As used herein, an "enterprise system" includes a system associated with at least one enterprise. Thus, the IT infrastructure 110 may include portions of systems operated, owned or otherwise controlled or associated with two or more enterprises or other entities.

The network 106 is assumed to comprise a global computer network such as the Internet, although other types of networks can be part of the network 106, including a wide area network (WAN), a local area network (LAN), a satellite network, a telephone or cable network, a cellular network, a wireless network such as a WiFi or WiMAX network, or various portions or combinations of these and other types of networks.

The telemetry database 108, as discussed above, is configured to store and record information relating to the IT infrastructure 110, such as telemetry or other time series data that is produced or associated with assets of the IT infrastructure 110. In some embodiments, the telemetry data is assumed to comprise univariate time series data as described in further detail below. The telemetry database 108 in some embodiments is implemented using one or more storage systems or devices associated with the enterprise SOC 102 or the IT infrastructure 110. In some embodiments, one or more of the storage systems utilized to implement the telemetry database 108 comprises a scale-out all-flash content addressable storage array or other type of storage array.

The term "storage system" as used herein is therefore intended to be broadly construed, and should not be viewed as being limited to content addressable storage systems or flash-based storage systems. A given storage system as the term is broadly used herein can comprise, for example, network-attached storage (NAS), storage area networks (SANs), direct-attached storage (DAS) and distributed DAS, as well as combinations of these and other storage types, including software-defined storage.

Other particular types of storage products that can be used in implementing storage systems in illustrative embodiments include all-flash and hybrid flash storage arrays, software-defined storage products, cloud storage products, object-based storage products, and scale-out NAS clusters. Combinations of multiple ones of these and other storage products can also be used in implementing a given storage system in an illustrative embodiment.

Although not explicitly shown in FIG. 1, one or more input-output devices such as keyboards, displays or other types of input-output devices may be used to support one or more user interfaces to the enterprise SOC 102, the client devices 104, the telemetry database 108, and the IT infrastructure 110, as well as to support communication between the enterprise SOC 102, client devices 104, telemetry database 108, IT infrastructure 110 and other related systems and devices not explicitly shown.

In the present embodiment, alerts or notifications generated by a threat detection and remediation system 112 of the enterprise SOC 102 are provided over network 106 to client devices 104, or to a system administrator, information technology (IT) manager, or other authorized personnel via one or more host agents. Such host agents may be implemented via the client devices 104 or by other computing or processing devices associated with a system administrator, IT manager or other authorized personnel. Such devices can illustratively comprise mobile telephones, laptop computers, tablet computers, desktop computers, or other types of computers or processing devices configured for communication over network 106 with the enterprise SOC 102 and the threat detection and remediation system 112. For example, a given host agent may comprise a mobile telephone equipped with a mobile application configured to receive alerts from the enterprise SOC 102 or the threat detection and remediation system 112 and to provide an interface for the host agent to select particular remedial measures for responding to the alert or notification. Examples of such remedial measures may include blocking access by one or more of the client devices 104 to the IT infrastructure 110 or assets thereof, requiring user input or authentication by the client devices 104 to obtain information from or otherwise utilize one or more resources or assets of the IT infrastructure 110, triggering further review of the IT infrastructure 110 or resources or assets thereof, etc. Further examples of remedial measures or actions will be described below.

It should be noted that a "host agent" as this term is generally used herein may comprise an automated entity, such as a software entity running on a processing device. Accordingly, a host agent need not be a human entity.

As shown in FIG. 1, the enterprise SOC 102 comprises the threat detection and remediation system 112. As will be described in further detail below, the threat detection and remediation system 112 is configured to monitor the IT infrastructure 110 through analysis of telemetry data produced by or associated with assets of the IT infrastructure 110.

Although shown as an element of the enterprise SOC 102 in this embodiment, the threat detection and remediation system 112 in other embodiments can be implemented at least in part externally to the enterprise SOC 102, for example, as a stand-alone server, set of servers or other type of system coupled to the network 106. In some embodiments, the threat detection and remediation system 112 may be implemented at least in part within one or more of the client devices 104.

The threat detection and remediation system 112 in the FIG. 1 embodiment is assumed to be implemented using at least one processing device. Each such processing device generally comprises at least one processor and an associated memory, and implements one or more functional modules for controlling certain features of the threat detection and remediation system 112. In the FIG. 1 embodiment, the threat detection and remediation system 112 comprises a telemetry data parsing module 114, machine learning-based missing value imputation module 116, and a remedial action initiation module 118.

The telemetry data parsing module 114 is configured to obtain a time series dataset (e.g., from the telemetry database 108, from assets in the IT infrastructure 110, from monitoring tools associated with assets in the IT infrastructure 110), and to determine that the obtained time series dataset has one or more missing values. The obtained time series dataset is assumed to comprise monitoring data associated with one or more of the assets in the IT infrastructure 110.

The machine learning-based missing value imputation module 116 is configured to generate, utilizing a machine learning algorithm, a reconstructed time series dataset having one or more imputed values for the one or more missing values in the obtained time series dataset, the machine learning algorithm comprising a generative network implementing inverse network parameter determination for network parameters of the generative network. In some embodiments, the machine learning algorithm comprises a convolutional neural network (CNN) initialized with randomized values for the network parameters.

The remedial action initiation module 118 is configured to classify one or more patterns in the obtained time series dataset utilizing the reconstructed time series dataset, to select one or more remedial actions for controlling at least one of the one or more assets based at least in part on the classified one or more patterns in the obtained time series dataset, and to initiate the selected one or more remedial actions to control the at least one asset.

The type of remedial action depends on the type of telemetry data being analyzed. For example, if the telemetry data is associated with health of a hardware or software asset in the IT infrastructure 110, analysis of the reconstructed telemetry data may be utilized to determine whether the hardware or software asset is in poor health and may take appropriate action. Poor health of a hardware or software asset may refer to a situation in which the hardware or software asset is likely to fail. For a hardware asset such as computing device, the poor health may be indicative of failure or errors encountered by physical components thereof. Consider, as an example, a storage system which is in poor health due to a lack of available storage capacity. In such an instance, the remedial action may include freeing up space on the storage system (such as by backing up data, clearing out old data, deleting data, etc.), deploying or allocating additional storage resources to the storage system, etc. Various other examples are possible. For a software asset, the poor health may be indicative of malware or adware that is infecting the software (e.g., an operating system, one or more applications, etc.). In such an instance, the remedial action may include applying security hardening procedures (e.g., running a virus, malware or adware scanning tool, patching vulnerabilities, etc.), blocking access to that software, causing the software to be run in a sandboxed execution environment, etc.

It should be noted that the assets producing telemetry data are not limited to the above-described types of hardware and software assets. Consider, as another example, telemetry data produced by health monitoring devices (e.g., fitness trackers, wearable devices, physiological sensors, etc.). In such an instance, the threat detection and remediation system 112 may be implemented within a health care or health monitoring system, rather than within enterprise SOC 102. When missing values are imputed using the techniques described herein, the reconstructed signals may be analyzed to detect conditions to be remediated. For example, the reconstructed signals may be analyzed to identify a health condition of an end-user that is associated with a given health monitoring device. On detecting a potentially harmful health condition, the remedial action initiated by the remedial action initiation module 118 of the threat detection and remediation system 112 may include applying some type of therapy to the end-user (e.g., administering medicine thereto), contacting medical professionals or first responders, etc. Various other examples are possible.

Consider, as a further example, signals transmitted between nodes in a communication network (e.g., signals transmitted between satellite nodes in a satellite communication network, where assets of the IT infrastructure 110 may include such satellite nodes and the network 106 provides the satellite communication network). In such an instance, the threat detection and remediation system 112 may be implemented within a network monitoring tool or within one of the nodes in the communication network for reconstructing received signals transmitted from other nodes. The remedial action initiated by the remedial action initiation module 118 in this case may be initiating some designated action based on the reconstructed signals transmitted between the nodes, including re-transmission of the reconstructed signals to another network node, where the other network node may be another node in the same network (e.g., another satellite node) or a node in another network (e.g., one or more end-user terminals), etc.

It is to be appreciated that the particular arrangement of the enterprise SOC 102, the threat detection and remediation system 112, the telemetry data parsing module 114, the machine learning-based missing value imputation module 116, and the remedial action initiation module 118 illustrated in the FIG. 1 embodiment is presented by way of example only, and alternative arrangements can be used in other embodiments. As discussed above, for example, the threat detection and remediation system 112, or portions thereof such as one or more of the telemetry data parsing module 114, the machine learning-based missing value imputation module 116, and the remedial action initiation module 118, may in some embodiments be implemented internal to one or more of the client devices 104 or the IT infrastructure 110. As another example, the functionality associated with the telemetry data parsing module 114, the machine learning-based missing value imputation module 116, and the remedial action initiation module 118 may be combined into one module, or separated across more than three modules with the multiple modules possibly being implemented with multiple distinct processors or processing devices.

At least portions of the telemetry data parsing module 114, the machine learning-based missing value imputation module 116, and the remedial action initiation module 118 may be implemented at least in part in the form of software that is stored in memory and executed by a processor.

It is to be understood that the particular set of elements shown in FIG. 1 for monitoring the IT infrastructure 110 utilizing analysis of telemetry data with missing values imputed utilizing machine learning is presented by way of illustrative example only, and in other embodiments additional or alternative elements may be used. Thus, another embodiment may include additional or alternative systems, devices and other network entities, as well as different arrangements of modules and other components.

By way of example, in other embodiments, the threat detection and remediation system 112 may be implemented external to enterprise SOC 102, such that the enterprise SOC 102 can be eliminated. As noted above, where the assets of the IT infrastructure 110 producing the telemetry data comprise health monitoring devices, the threat detection and remediation system 112 may be part of a health care or health monitoring system. In other embodiments, the threat detection and remediation system 112 may be part of or otherwise associated with another system other than the enterprise SOC 102, such as, for example, a critical incident response center (CIRC), a security analytics system, a security information and event management (SIEM) system, a Governance, Risk and Compliance (GRC) system, a network monitoring system, etc.

The enterprise SOC 102, threat detection and remediation system 112, and other portions of the system 100 may be part of cloud infrastructure as will be described in further detail below. The cloud infrastructure hosting the SOC 102 and/or the threat detection and remediation system 112 may also host one or more of the client devices 104, the telemetry database 108, at least a portion of the IT infrastructure 110, combinations thereof, etc.

The enterprise SOC 102 and other components of the information processing system 100 in the FIG. 1 embodiment are assumed to be implemented using at least one processing platform comprising one or more processing devices each having a processor coupled to a memory. Such processing devices can illustratively include particular arrangements of compute, memory, storage and network resources.

The enterprise SOC 102, client devices 104, telemetry database 108 and IT infrastructure 110 or components thereof may be implemented on respective distinct processing platforms, although numerous other arrangements are possible. For example, in some embodiments at least portions of the enterprise SOC 102 and one or more of the client devices 104 or IT infrastructure 110 are implemented on the same processing platform. A given one of the client devices 104 or the IT infrastructure 110 can therefore be implemented at least in part within at least one processing platform that implements at least a portion of the enterprise SOC 102, such as the threat detection and remediation system 112.

The term "processing platform" as used herein is intended to be broadly construed so as to encompass, by way of illustration and without limitation, multiple sets of processing devices and associated storage systems that are configured to communicate over one or more networks. For example, distributed implementations of the system 100 are possible, in which certain components of the system reside in one data center in a first geographic location while other components of the system reside in one or more other data centers in one or more other geographic locations that are potentially remote from the first geographic location. Thus, it is possible in some implementations of the system 100 for the enterprise SOC 102, client devices 104, telemetry database 108 and IT infrastructure 110, or portions or components thereof, to reside in different data centers. Numerous other distributed implementations are possible. The enterprise SOC 102 or portions thereof, such as the threat detection and remediation system 112, can also be implemented in a distributed manner across multiple data centers.

Additional examples of processing platforms utilized to implement the enterprise SOC 102 and other portions of the system 100 in illustrative embodiments will be described in more detail below in conjunction with FIGS. 6 and 7.

It is to be appreciated that these and other features of illustrative embodiments are presented by way of example only, and should not be construed as limiting in any way.

An exemplary process for reconstructing time series datasets with missing values utilizing machine learning will now be described in more detail with reference to the flow diagram of FIG. 2. It is to be understood that this particular process is only an example, and that additional or alternative processes for reconstructing time series datasets with missing values utilizing machine learning may be used in other embodiments.

In this embodiment, the process includes steps 200 through 208. These steps are assumed to be performed by the threat detection and remediation system 112 of the enterprise SOC 102 utilizing the telemetry data parsing module 114, the machine learning-based missing value imputation module 116, and the remedial action initiation module 118. The process begins with step 200, obtaining a time series dataset having one or more missing values, the time series dataset comprising monitoring data associated with one or more assets. The time series dataset may comprise a univariate time series dataset.

In step 202, a reconstructed time series dataset is generated utilizing a machine learning algorithm. The reconstructed time series dataset has one or more imputed values for the one or more missing values in the obtained time series dataset. The machine learning algorithm comprises a generative network implementing inverse network parameter determination for network parameters of the generative network. In some embodiments, the machine learning algorithm comprises a CNN initialized with randomized values for the network parameters, and step 202 may include performing one or more iterations of: applying the obtained time series dataset having the one or more missing values to the convolutional neural network to produce a candidate reconstructed time series dataset having one or more imputed values for the one or more missing values in the obtained time series dataset; and tuning the network parameters of the CNN using a loss function that compares the candidate reconstructed time series dataset with the obtained time series dataset. The loss function may comprise a sum of a variation loss and a regularization of the network parameters of the CNN. The CNN may comprise two or more layers each comprising two or more convolutional filters. The CNN may comprise at least a first layer that applies batch normalization and utilizes a rectified linear unit (ReLU) activation function, at least a second layer that does not apply batch normalization and utilizes a hyperbolic tangent (TanH) activation function, and at least a third layer that comprises a fully connected (FC) layer. The third layer may comprise a final layer of the CNN, with the CNN including two or more instances of the first layer and at least one instance of the second layer prior to the final layer.

Figure 2:
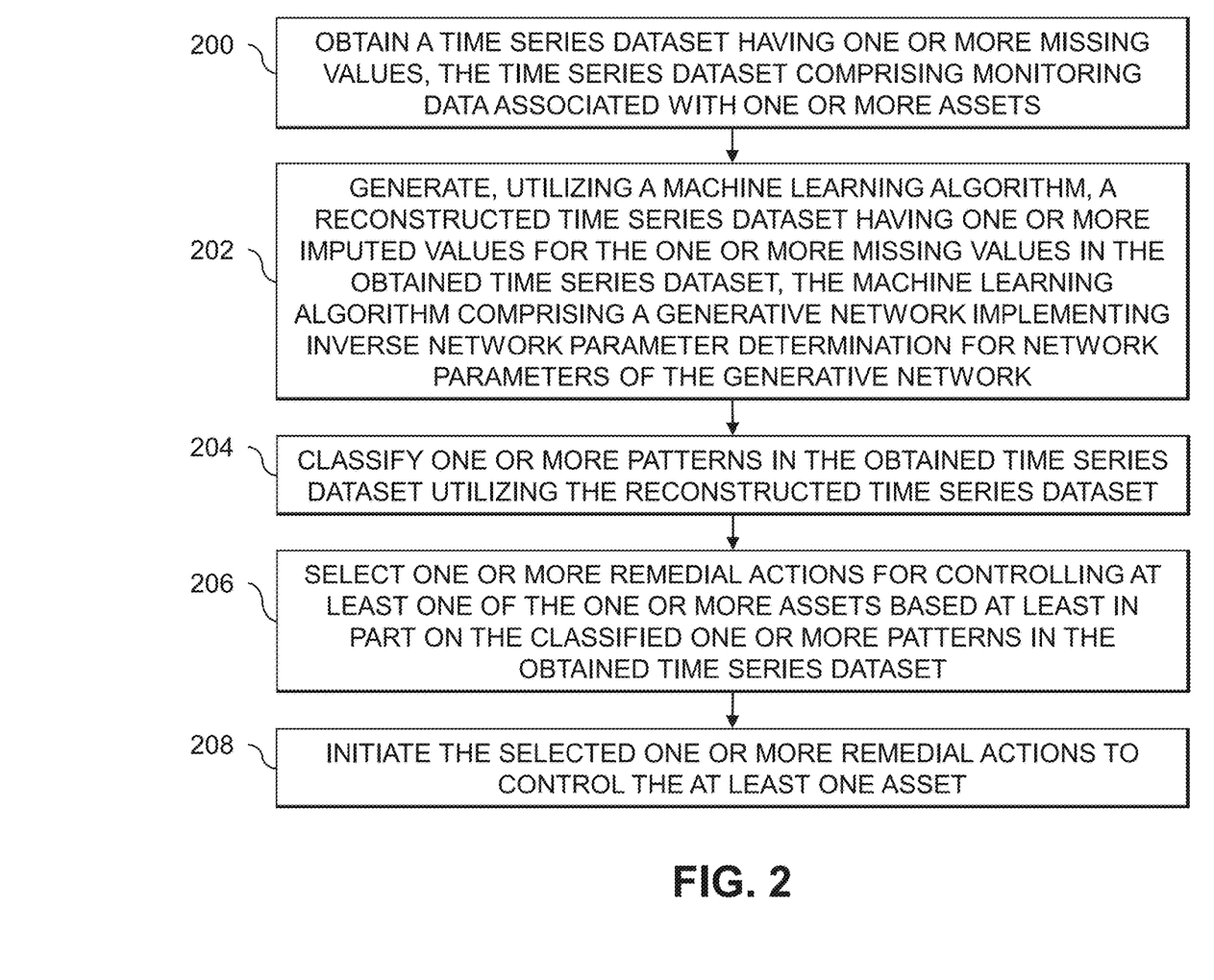
FIG. 2 is a flow diagram of an exemplary process for reconstructing time series datasets with missing values utilizing machine learning in an illustrative embodiment.

The FIG. 2 process continues with step 204, classifying one or more patterns in the obtained time series dataset utilizing the reconstructed time series dataset. Step 204 may include applying the reconstructed time series dataset as input to at least one additional machine learning algorithm. In step 206, one or more remedial actions are selected for controlling at least one of the one or more assets based at least in part on the classified one or more patterns in the obtained time series dataset. The selected one or more remedial actions are initiated in step 208 to control the at least one asset.

In some embodiments, the time series dataset comprises telemetry data associated with one or more assets. The one or more assets may comprise one or more computing resources in an IT infrastructure, the patterns classified in step 204 may characterize health of at least a given one of the one or more computing resources in the IT infrastructure, and the one or more remedial actions selected in step 206 may comprise at least one remedial action for modifying a configuration of the given computing resource. The one or more assets may alternatively comprise one or more health monitoring devices associated with at least one user, the patterns classified in step 204 may characterize one or more health conditions of the at least one user, and the one or more remedial actions selected in step 206 may comprise at least one remedial action for alerting the at least one user to the one or more health conditions. The one or more assets may alternatively comprise two or more nodes in a communication network, the one or more patterns classified in step 204 may characterize transmission of one or more signals between the two or more nodes in the communication network, and the one or more remedial actions selected in step 206 may comprise re-transmission of the reconstructed time series dataset with the one or more imputed values to at least one additional node in the communication network.

Synthetic data generation is an evolving area of imputation research, with various applications including in signal processing, computer vision, natural language processing, etc. Illustrative embodiments provide techniques for the imputation of missing data points within a time series dataset, where the time series dataset may comprise a univariate time series dataset. For example, the techniques described herein may be used for imputation of missing data points in telemetry data. In some embodiments, a novel CNN is used to impute missing values in a dataset using an inverse network parameter optimization method. As described in further detail below, the techniques described herein outperform conventional approaches such as algorithms using Lasso and mean imputation commonly used in signal processing and data science, respectively. Lasso imputation is a shrinkage and selection method for linear regression, which minimizes the usual sum of square errors with a bound on the sum of the absolute values of the coefficients. The techniques described herein provide a robust approach to the imputation of missing values, including in univariate time series datasets such as that obtained from telemetry data (e.g., from assets in an IT infrastructure, from health monitoring devices, satellite signals, etc.).

Time series data can be found in many domains, including biology, electrical engineering, finance, information processing systems including IT infrastructure, health monitoring systems, satellite systems, etc. Whenever data is recorded, it is inevitable that missing values will occur. Missing values may be a result of failure to measure, incomplete data capture, accidental or intentional deletion of data, etc. Missing values need to be imputed with reasonable values to enable many machine learning algorithms to utilize a dataset, as machine learning algorithms typically rely on complete datasets. Consider, as an example, an operator of an IT infrastructure (e.g., a data center, a cloud computing platform, etc.) that seeks to deliver value for end-users with minimal burden on the end-users. To minimize the end-user burden, the operator of the IT infrastructure may routinely collect hardware and software health data (e.g., for assets of the IT infrastructure) to ensure that the end user's hardware and software is performing efficiently and will avoid unwanted catastrophic system failure (e.g., crash, the so-called blue screen of death, etc.). Such hardware and software data is often streamed to the operator of the IT infrastructure (e.g., or to a monitoring system implemented internal or external to the IT infrastructure) in a process referred to as telemetry. For such telemetry data, missing values need to be imputed with reasonable values to enable many machine learning algorithms to work. Thus, complete telemetry datasets are essential for data science teams that develop and maintain machine learning algorithms to predict and prevent system failures.

There are two general approaches for confronting missing values in a dataset: (1) removing all data entries in the dataset associated with the missing values; and (2) imputing the missing values. Missing data can be imputed using various techniques, including mean-filling, filling with the last known observation, interpolating between known observations, etc. Mean-filling and filling with the last known observations are common techniques in the data science community, yet these approaches do not consider the overall pattern of the data and can thus lead to suboptimal outcomes. Conversely, interpolation techniques consider the immediately preceding and succeeding values and have proven useful when imputing missing values in univariate time series data using linear, spline and nearest-neighbor methods. For example, Lasso interpolation techniques may be utilized. Recent advances have led to generative adversarial networks (GAN) and deep learning-based imputation methods, but such approaches are typically used for multivariate data imputation.

A CNN model is a trainable, non-linear machine learning algorithm that typically operates on images at the pixel level, and learns low-level features and high-level representations in an integrated manner. CNN models can learn optimal shift invariant local feature detectors while maintaining invariance to geometric distortions of the input image due to their shared structure of weights and multiple network layers. Image embeddings based on the activations of CNNs have become a dominant method in image retrieval due to their discriminative power and compact representation. CNN-based image embeddings may be used to recreate input images in a process referred to as inversion. Deep Image Prior (DIP) is an extension of such methods. A fundamental weakness of prototypical deep learning is that it requires extensive training on labeled data to work well. Historically, large CNN performance increases for image reconstruction tasks were only possible due to millions of training images. In contrast, the DIP approach utilizes an untrained randomly-initialized shallow CNN to optimize network parameters θ by minimizing the difference (e.g., using a loss function) between a damaged input image $\acute{s}$ and a restored output image $\hat{s}$. As formulated in Equation 1, $\acute{s}$ is created by a CNN $f_\theta(\cdot)$ where E($\cdot$) is a task-dependent data term and p is an image embedding:

$$\hat{s} = \underset{\theta}{\operatorname{argmin}} E(f_\theta(p); \acute{s}) \quad (1)$$

A combination of early stopping, the proper network architecture, and the correct network learning hyperparameters can lead to a restored (e.g., super-resolution or denoised) output $\hat{s}$ from a damaged input $\acute{s}$ using DIP. Early-stopping is an important principle in DIP because it is easier for a CNN to capture high-level features of an image rather than high-frequency noise. Therefore, when the CNN converges to a clean output $\acute{s}$ first, where $\hat{s} \sim s^*$, and then adds noise during later iterations in an attempt to faithfully reproduce the damaged input $\acute{s}$ such that $\hat{s} \sim \acute{s}$.

A variety of missing-value imputation problems can be discretized to a linear system where y∈ $\mathbb{R}^m$ is the measured data, A∈ $\mathbb{R}^{m \times n}$ is the forward operator or measurement matrix, and x∈X⊂ $\mathbb{R}^n$ is the object being probed by applying A as shown in Equation 2 below:

$$y = Ax \quad (2)$$

Depending on the application, a set of plausible reconstructions or imputations of x could model univariate time series signals. In many cases the resulting problem is ill-posed, due to either poor conditioning of A or m<<n. A typical approach to solve ill-posed problems of this type is to minimize a $\ell_1$ normalized objective function, as exemplified by the Lasso algorithm. DIP-based approaches demonstrate additional benefits over Lasso, with strong resistance to noise and rapid convergence when reconstructing missing signals.

Figure 3:
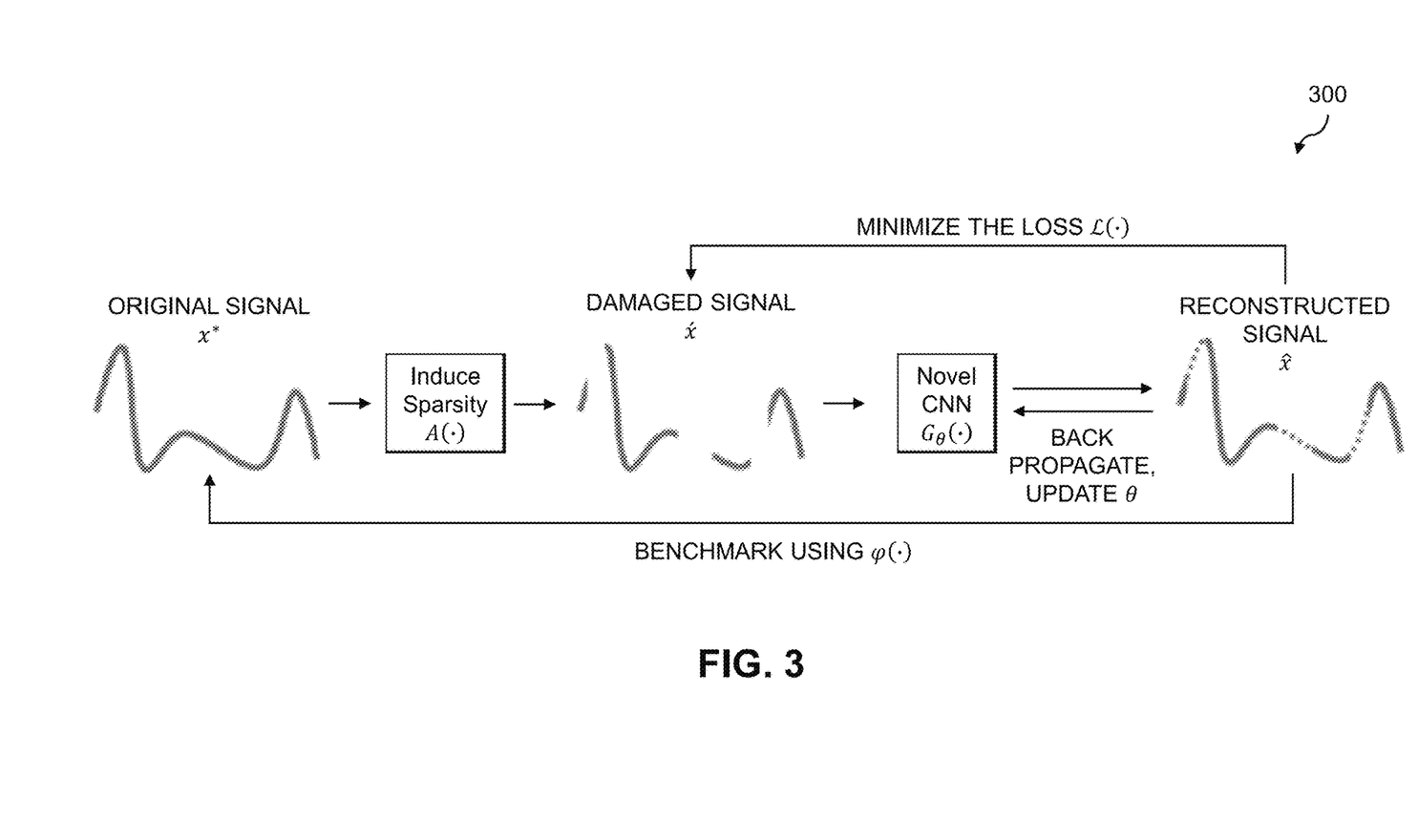
FIG. 3 shows a framework of a convolutional neural network for imputing missing values in time series datasets in an illustrative embodiment.

In some embodiments, the following approach is utilized. A complete signal vector $x^* \in \mathbb{R}^j$ is assumed to be damaged such that it is missing k values, where k<<j, and the damaged vector is termed $\acute{x}$. The measurement matrix is defined as A∈ $\mathbb{R}^{m \times j}$. Given A and the observations y=A$\acute{x}$, the goal is to find a reconstruction $\hat{x}$ as similar to $x^*$ as possible. This is illustrated in FIG. 3, which shows a framework 300 for a novel CNN imputation method $G_\theta(\cdot)$ where the loss between the damaged signal $\acute{x}$ and the output of $G_\theta(\cdot)$, $\hat{x}$, was minimized in order to optimize θ, and thus, optimize $\hat{x}$. The optimized output $\hat{x}$ is compared against the original complete signal x* to benchmark performance as described in further detail below.

A generative model is defined by a deterministic function $G(\cdot): \mathbb{R}^k \to \mathbb{R}^j$ that takes $z \in \mathbb{R}^k$ as an input to generate $G(z) \in \mathbb{R}^j$. Vector z is initialized in some embodiments as a 32-dimensional vector filled with values of a standard normal distribution ($\mu=0$, $\sigma=1$). The novel CNN described herein, denoted as $G_\theta(z)$, may be referred to herein as a "naïve" CNN, as it is initiated as an untrained CNN with randomized network parameters $\theta$. Typically, $k \ll j$, where the generative model is mapped from a low-dimensional representation space to a high-dimensional sample space. The approach used in some embodiments finds a vector in the representation space such that the corresponding vector in the sample space matches the observed measurements. Thus, the objective is defined as minimizing the loss $\mathcal{L}(\cdot)$ as shown in Equation 3:

$$\mathcal{L}(z) = \|AG_\theta(z) - y\|_{\ell_2}^2 \quad (3)$$

$\mathcal{L}(z)$ may be minimized with an optimization procedure. In particular, when the generative model $G_\theta(\cdot)$ is differentiable, the gradients of $\mathcal{L}(\cdot)$ may be evaluated with respect to z using backpropagation and gradient-based optimizers. If the optimization procedure terminated at $\hat{z}$, the reconstruction of x* is $G_\theta(\hat{z})$. The measurement error may be defined as $\|AG_\theta(\hat{z}) - y\|_{\ell_2}^2$ and the reconstruction error may be defined as $\|G_\theta(\hat{z}) - x^*\|_{\ell_2}^2$.

Further, the algorithm may be recast as an optimization of network parameters $\theta \in \mathbb{R}^d$ for the novel CNN $G_\theta(z)$, where $\theta^*$ are the network parameters that correspond to the reconstructed signal $\hat{x}$ as shown in Equation 4:

$$\theta^* = \underset{\theta}{\operatorname{argmin}} \|y - G_\theta(z)\|_{\ell_2}^2 \quad (4)$$

Regularizing the network output has demonstrated superiority over mean-squared error (MSE) loss optimization for DIP-based methods. Thus, some embodiments utilize a regularization component $\mathcal{L}_R(z; \theta)$ in the loss function of the novel CNN as shown in Equation 5:

$$\theta^* = \underset{\theta}{\operatorname{argmin}} \{\|y - AG_\theta(z)\|_{\ell_2}^2 + \mathcal{L}_R(z; \theta)\} \quad (5)$$

The regularized loss function $\mathcal{L}_R(z; \theta)$ shown in Equation 6 is the sum of the total variation loss $\mathcal{L}_T(\cdot)$ shown in Equation 7 and the regularization of the network parameters $\mathcal{L}_w(\theta)$ shown in Equation 8. The tuning parameter $\lambda_T \in \mathbb{R}$ controls the amount of regularization induced by $\mathcal{L}_T(\cdot)$, and $\lambda_w \in$ is a tuning parameter that controls the amount of regularization induced by $\mathbb{R}_w(\cdot)$:

$$\mathcal{L}_R(z; \theta) = \lambda_T \mathcal{L}_T(G_\theta(z)) + \lambda_w \mathcal{L}_w(\theta) \quad (6)$$

$$\mathcal{L}_t(x) = \sum_{i=2}^{n} |x_i - x_{i-1}| \quad (7)$$

The network $G_\theta(\cdot)$ includes L layers where each network layer $l \in L$. The regularization of the network parameters $\mathcal{L}(\theta)$ involves the creation of a zero-filled vector $\{\vec{0}\}$ where the vector is of equal length to $\theta_i$, $|\theta_i| = |\{\vec{0}\}|$, $\forall i$ as shown in Equation 8. The summation of the $\ell_1$ norm of the fast Fourier transform (FFT) $\mathfrak{F}(\cdot)$ of the concatenated $\theta_i$ and $\{\vec{0}\}$ vectors, $\forall i$, results in $\mathcal{L}_w(\theta)$. The $\{\vec{0}\}$ vector fulfills the role of the imaginary values in the FFT calculation:

$$\mathcal{L}_w(\theta) = \sum_{i=0}^{L-1} \|\mathcal{F}\theta_i \oplus \vec{0}\|_{\ell_1} \quad (8)$$

At a high level, the novel CNN produces an n-dimensional output $G_\theta(z)$. Linear measurements are performed, given by $A \in \mathbb{R}^{m \times n}$, on the output to simulate m-dimensional measurements. The loss is then optimized using Equation 6 between the simulated measurements $AG_\theta(z)$ and the observed measurements $y=A\hat{x}$. The goal is to construct a signal output $\hat{x}=G_{\theta^*}(z)$ of the optimized final network that matches the original signal x* as closely as possible. During the optimization of $G_\theta(z)$, the latent vector z is held to a random initial value as the network parameters $\theta$ are optimized.

In a sample implementation, a shallow CNN architecture was used with one channel, L=10 layers, and 16 convolutional filters per layer l. Layers 1-7 and 9 of the CNN were $\ell_1$ batch normalized and utilized a ReLU activation function. Layer 8 of the CNN was not normalized, and utilized a TanH activation function. Layer 10 of the CNN, the final layer l=10 of the network, is an FC layer. The RMSprop optimizer was employed and its parameters were selected using a grid search over a fixed set of possible values. The optimizer hyperparameters included a learning rate of $10^{-4}$, momentum of 0.9, and a weight decay of 1 to optimize $\theta$. To tune the total variation loss $\mathcal{L}_T(\cdot)$ in Equation 7 a value of $\lambda_T=0.1$ was chosen and to tune the network parameter loss $L_w(\cdot)$ in Equation 8 a value of $\lambda_w=0.01$ was chosen. Early stopping was implemented by optimizing $\theta$ for only 3,000 iterations. It should be noted that this sample implementation of network hyperparameters is merely an example, and that embodiments are not limited to these particular values. In other embodiments, a different CNN architecture (e.g., with a different number of layers and convolutional filters, with different activation functions, with different parameter values, etc.) may be used.

The data imputation capabilities of the novel CNN imputation architecture described herein were explored by generating missing values at random (e.g., inducing sparsity) within a complete signal processing univariate time series dataset. Each signal $x_i^*$ contained 20 data points over discrete and equivalent timesteps j, where j was an integer and $j \in [0,19]$. The $x_i^*$ signals were treated as normalized vectors where $x_i^* \in [-1,1]$, and thus $\hat{x}_i \in [-1,1]$, and the $x_i^*$, $\hat{x}_i$ and $\hat{x}_i$ vectors were of equal length, $|x_i^*|=|\hat{x}_i|=|\hat{x}_i|$. The goal is to solve the inverse problem of recovering a signal $\ddot{x}$ that is an approximate match to the true signal x*.

To test the novel CNN method, 93 signal processing attributes recorded over 20 timesteps were analyzed, where the attributes were available from an internal dataset of 38,900 samples. The complete dataset, with no missing values, was utilized to generate random sparsity (e.g., a damaged signal $\hat{x}$) to allow benchmarking of the reconstructed (e.g., the imputed) signal $\hat{x}$ against the original complete signal x*. A matrix mask A was utilized to create the data sparsity in x* at random. To keep the imputation method as general as possible, domain knowledge of the signal attributes was not utilized.

Figure 4:
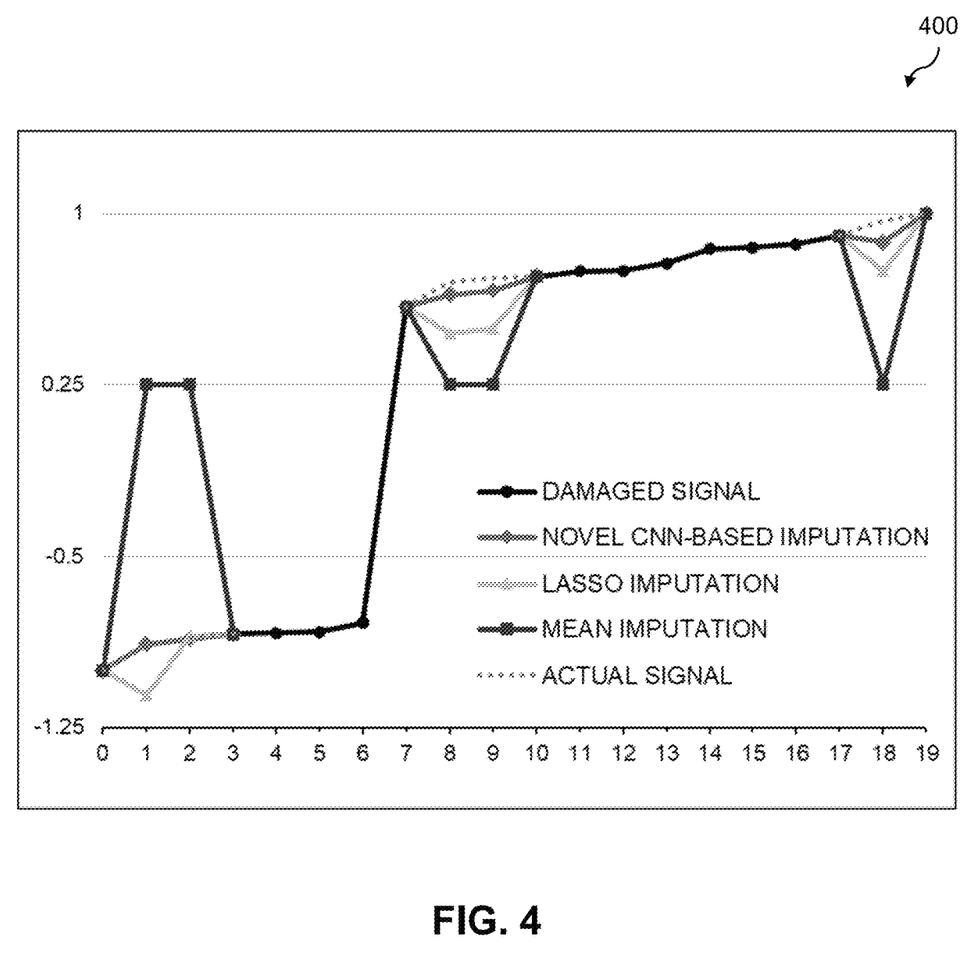
FIG. 4 shows a plot illustrating reconstruction of a time series data set using various methods in an illustrative embodiment.

The results of the novel CNN model were compared against two benchmark algorithms, a Lasso algorithm and mean imputation. In particular, the scikit-learn implementation of Lasso was utilized. The initial analysis included comparisons of the three imputation methods on a single signal to visualize the results. This is shown in the plot 400 of FIG. 4, which shows the actual signal, the damaged signal, and the reconstructions obtained using the novel CNN method, Lasso imputation, and mean imputation. The plot 400 shows the comparison of the reconstructed signal $\hat{x}$ for each imputation method for a damaged signal $\acute{x}$ that is missing 25% of its values (defined by (j−k)/j). As illustrated in the plot 400, the novel CNN imputation method faithfully reproduced the actual values of the original complete signal x*.

The high-level signal reconstruction performance of each algorithm was determined by calculating the cosine similarity $\phi_i$ of $\hat{x}_i$ and $x_i^*$. As shown in Equation 9, the cosine similarity $\phi_i \in [-1,1]$ was determined by an inner product (e.g., a dot product), which was commutative:

$$\phi_i = (x_i^* \cdot \hat{x}_i) = x_i^* \hat{x}_i^T = \Sigma_j (x_{ij}^* \times x_{ij}) \qquad (9)$$

A result of $\phi_i=1$ indicates that the two vectors, $x_i^*$ and $\hat{x}_i$, are identical.

Figure 5:
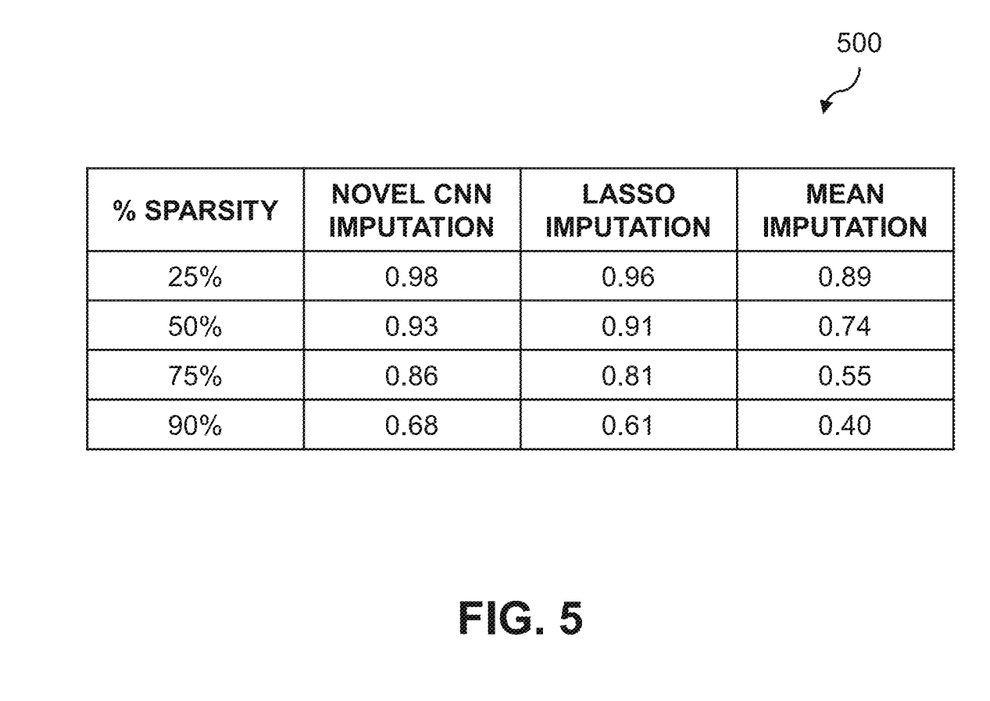
FIG. 5 shows a table illustrating reconstruction performance using various methods in an illustrative embodiment.

The ability of the imputation methods to reconstruct $\hat{x}_i$ from a damaged signal $\acute{x}_i$ that contained missing values at different induced sparsity levels (e.g., 25%, 50%, 75% and 90%) of the original complete signal $x_i^*$ is also evaluated. FIG. 5 shows a table 500, illustrating the average φ value for each imputation method (e.g., the novel CNN imputation method, the Lasso imputation method, and the mean imputation method), where every signal in the dataset (with n=38,900) was induced with different percentage sparsity (e.g., with values of 25%, 50%, 75% and 90%). A value of φ=1 represents a perfect reconstruction of the original complete signal x* (e.g., where x*=2). The best result for each percentage sparsity is the novel CNN-based imputation method described herein, demonstrating that the novel CNN-based imputation method described herein is superior to the Lasso and mean imputation methods at all levels of induced sparsity.

The novel CNN-based imputation method described herein provides an efficient approach for imputing missing values in time series datasets, including in univariate time series signal processing datasets. In some embodiments, the novel CNN-based imputation method utilizes a CNN as a generative network to reconstruct a damaged signal. This unique generative framework, coupled with a unique loss function, effectively reconstructs damaged signals (e.g., damaged telemetry signals) with superior results relative to conventional approaches such as Lasso and mean imputation. Thus, the techniques described herein provide a robust approach to the imputation of missing values in univariate time series datasets.

It is to be appreciated that the particular advantages described above and elsewhere herein are associated with particular illustrative embodiments and need not be present in other embodiments. Also, the particular types of information processing system features and functionality as illustrated in the drawings and described above are exemplary only, and numerous other arrangements may be used in other embodiments.

Illustrative embodiments of processing platforms utilized to implement functionality for reconstructing time series datasets with missing values utilizing machine learning will now be described in greater detail with reference to FIGS. 6 and 7. Although described in the context of system 100, these platforms may also be used to implement at least portions of other information processing systems in other embodiments.

Figure 6:
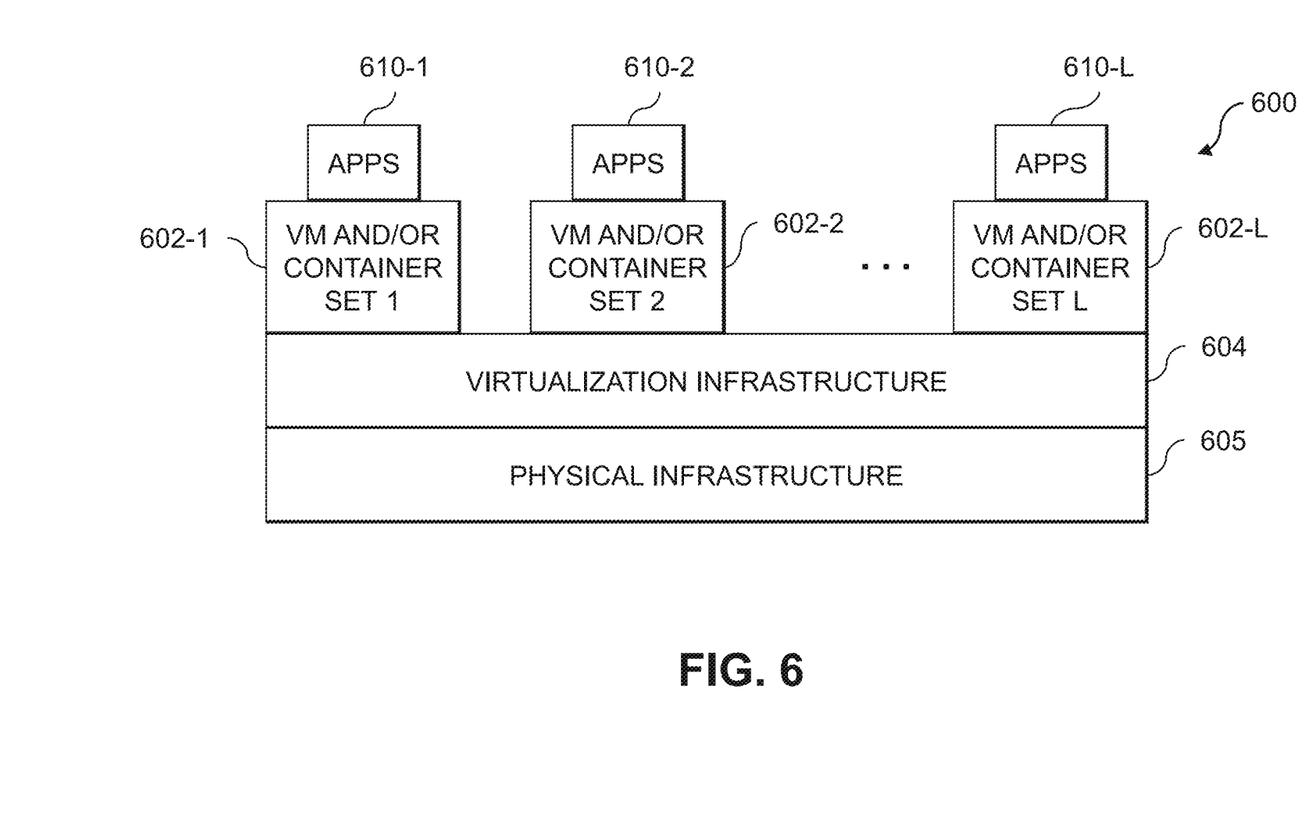
FIGS. 6 and 7 show examples of processing platforms that may be utilized to implement at least a portion of an information processing system in illustrative embodiments.
Figure 7:
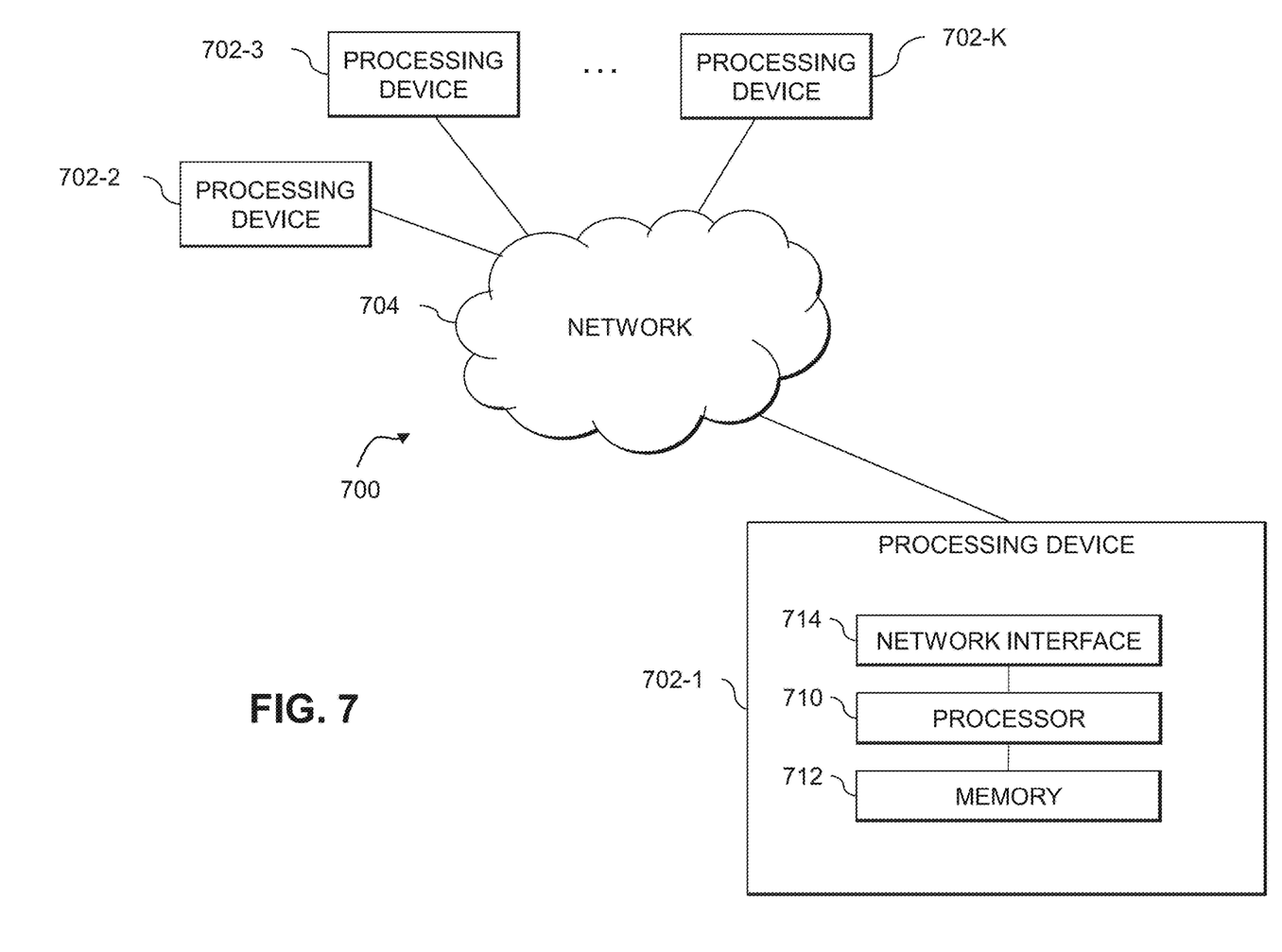

FIG. 6 shows an example processing platform comprising cloud infrastructure 600. The cloud infrastructure 600 comprises a combination of physical and virtual processing resources that may be utilized to implement at least a portion of the information processing system 100 in FIG. 1. The cloud infrastructure 600 comprises multiple virtual machines (VMs) and/or container sets 602-1, 602-2, . . . 602-L implemented using virtualization infrastructure 604. The virtualization infrastructure 604 runs on physical infrastructure 605, and illustratively comprises one or more hypervisors and/or operating system level virtualization infrastructure. The operating system level virtualization infrastructure illustratively comprises kernel control groups of a Linux operating system or other type of operating system.

The cloud infrastructure 600 further comprises sets of applications 610-1, 610-2, . . . 610-L running on respective ones of the VMs/container sets 602-1, 602-2, . . . 602-L under the control of the virtualization infrastructure 604. The VMs/container sets 602 may comprise respective VMs, respective sets of one or more containers, or respective sets of one or more containers running in VMs.

In some implementations of the FIG. 6 embodiment, the VMs/container sets 602 comprise respective VMs implemented using virtualization infrastructure 604 that comprises at least one hypervisor. A hypervisor platform may be used to implement a hypervisor within the virtualization infrastructure 604, where the hypervisor platform has an associated virtual infrastructure management system. The underlying physical machines may comprise one or more distributed processing platforms that include one or more storage systems.

In other implementations of the FIG. 6 embodiment, the VMs/container sets 602 comprise respective containers implemented using virtualization infrastructure 604 that provides operating system level virtualization functionality, such as support for Docker containers running on bare metal hosts, or Docker containers running on VMs. The containers are illustratively implemented using respective kernel control groups of the operating system.

As is apparent from the above, one or more of the processing modules or other components of system 100 may each run on a computer, server, storage device or other processing platform element. A given such element may be viewed as an example of what is more generally referred to herein as a "processing device." The cloud infrastructure 600 shown in FIG. 6 may represent at least a portion of one processing platform. Another example of such a processing platform is processing platform 700 shown in FIG. 7.

The processing platform 700 in this embodiment comprises a portion of system 100 and includes a plurality of processing devices, denoted 702-1, 702-2, 702-3, . . . 702-K, which communicate with one another over a network 704.

The network 704 may comprise any type of network, including by way of example a global computer network such as the Internet, a WAN, a LAN, a satellite network, a telephone or cable network, a cellular network, a wireless network such as a WiFi or WiMAX network, or various portions or combinations of these and other types of networks.

The processing device 702-1 in the processing platform 700 comprises a processor 7710 coupled to a memory 712.

The processor 710 may comprise a microprocessor, a microcontroller, an application-specific integrated circuit (ASIC), a field-programmable gate array (FPGA), a central processing unit (CPU), a graphical processing unit (GPU), a tensor processing unit (TPU), a video processing unit (VPU) or other type of processing circuitry, as well as portions or combinations of such circuitry elements.

The memory 712 may comprise random access memory (RAM), read-only memory (ROM), flash memory or other types of memory, in any combination. The memory 712 and other memories disclosed herein should be viewed as illustrative examples of what are more generally referred to as "processor-readable storage media" storing executable program code of one or more software programs.

Articles of manufacture comprising such processor-readable storage media are considered illustrative embodiments. A given such article of manufacture may comprise, for example, a storage array, a storage disk or an integrated circuit containing RAM, ROM, flash memory or other electronic memory, or any of a wide variety of other types of computer program products. The term "article of manufacture" as used herein should be understood to exclude transitory, propagating signals. Numerous other types of computer program products comprising processor-readable storage media can be used.

Also included in the processing device 702-1 is network interface circuitry 714, which is used to interface the processing device with the network 704 and other system components, and may comprise conventional transceivers.

The other processing devices 702 of the processing platform 700 are assumed to be configured in a manner similar to that shown for processing device 702-1 in the figure.

Again, the particular processing platform 700 shown in the figure is presented by way of example only, and system 100 may include additional or alternative processing platforms, as well as numerous distinct processing platforms in any combination, with each such platform comprising one or more computers, servers, storage devices or other processing devices.

For example, other processing platforms used to implement illustrative embodiments can comprise converged infrastructure.

It should therefore be understood that in other embodiments different arrangements of additional or alternative elements may be used. At least a subset of these elements may be collectively implemented on a common processing platform, or each such element may be implemented on a separate processing platform.

As indicated previously, components of an information processing system as disclosed herein can be implemented at least in part in the form of one or more software programs stored in memory and executed by a processor of a processing device. For example, at least portions of the functionality for reconstructing time series datasets with missing values utilizing machine learning as disclosed herein are illustratively implemented in the form of software running on one or more processing devices.

It should again be emphasized that the above-described embodiments are presented for purposes of illustration only. Many variations and other alternative embodiments may be used. For example, the disclosed techniques are applicable to a wide variety of other types of information processing systems, telemetry or time series datasets, etc. Also, the particular configurations of system and device elements and associated processing operations illustratively shown in the drawings can be varied in other embodiments. Moreover, the various assumptions made above in the course of describing the illustrative embodiments should also be viewed as exemplary rather than as requirements or limitations of the disclosure. Numerous other alternative embodiments within the scope of the appended claims will be readily apparent to those skilled in the art.

What is claimed is:

1. An apparatus comprising:
   at least one processing device comprising a processor coupled to a memory;
   the at least one processing device being configured to perform steps of:
   obtaining a time series dataset having one or more missing values, the time series dataset comprising monitoring data associated with one or more assets;
   generating, utilizing a machine learning algorithm, a reconstructed time series dataset having one or more imputed values for the one or more missing values in the obtained time series dataset, the machine learning algorithm comprising a generative network implementing inverse network parameter determination for network parameters of the generative network;
   classifying one or more patterns in the obtained time series dataset utilizing the reconstructed time series dataset;
   selecting one or more remedial actions for controlling at least one of the one or more assets based at least in part on the classified one or more patterns in the obtained time series dataset; and
   initiating the selected one or more remedial actions to control the at least one asset;
   wherein the machine learning algorithm comprises a convolutional neural network; and
   wherein generating the reconstructed time series dataset having the one or more imputed values comprises performing two or more iterations of:
   applying the obtained time series dataset having the one or more missing values to the convolutional neural network to produce a candidate reconstructed time series dataset having one or more imputed values for the one or more missing values in the obtained time series dataset; and
   tuning network parameters of the convolutional neural network using a loss function that compares the candidate reconstructed time series dataset with the obtained time series dataset.

2. The apparatus of claim 1 wherein the time series dataset comprises a univariate time series dataset.

3. The apparatus of claim 1 wherein the convolutional neural network is initialized with randomized values for the network parameters.

4. The apparatus of claim 1 wherein the loss function comprises a sum of a variation loss and a regularization of the network parameters of the convolutional neural network.

5. The apparatus of claim 1 wherein the convolutional neural network comprises two or more layers each comprising two or more convolutional filters.

6. The apparatus of claim 1 wherein the convolutional neural network comprises:
   at least a first layer that applies batch normalization and utilizes a rectified linear unit activation function;
   at least a second layer that does not apply batch normalization and utilizes a hyperbolic tangent activation function; and
   at least a third layer that comprises a fully connected layer.

7. The apparatus of claim 6 wherein the third layer comprises a final layer of the convolutional neural network, and wherein the convolutional neural network comprise two or more instances of the first layer and at least one instance of the second layer prior to the final layer.

8. The apparatus of claim 1 wherein classifying one or more patterns in the obtained time series dataset utilizing the reconstructed time series dataset comprises applying the reconstructed time series dataset as input to at least one additional machine learning algorithm.

9. The apparatus of claim 1 wherein the time series dataset comprises telemetry data associated with the one or more assets.

10. The apparatus of claim 9 wherein the one or more assets comprise one or more computing resources in an information technology infrastructure.

11. The apparatus of claim 10 wherein the classified one or more patterns in the obtained time series dataset characterize health of at least a given one of the one or more computing resources in the information technology infrastructure, and wherein the selected one or more remedial actions comprise at least one remedial action for modifying a configuration of the given computing resource.

12. The apparatus of claim 9 wherein the one or more assets comprise one or more health monitoring devices associated with at least one user, wherein the classified one or more patterns in the obtained time series dataset characterize one or more health conditions of the at least one user, and wherein the selected one or more remedial actions comprise at least one remedial action for alerting the at least one user to the one or more health conditions.

13. The apparatus of claim 1 wherein the one or more assets comprise two or more nodes in a communication network, wherein the classified one or more patterns in the obtained time series dataset characterize transmission of one or more signals between the two or more nodes in the communication network, and wherein the selected one or more remedial actions comprise re-transmission of the reconstructed time series dataset with the one or more imputed values to at least one additional node in the communication network.

14. The apparatus of claim 1 wherein the loss function comprises a regularized loss function comprising a first tunning parameter controlling an amount of regularization induced by variation loss and a second tuning parameter controlling an amount of regularization induced by regularization of the network parameters of the convolutional neural network, and wherein a value of the first tuning parameter is greater than a value of the second tuning parameter.

15. A computer program product comprising a non-transitory processor-readable storage medium having stored therein program code of one or more software programs, wherein the program code when executed by at least one processing device causes the at least one processing device to perform steps of:
obtaining a time series dataset having one or more missing values, the time series dataset comprising monitoring data associated with one or more assets;
generating, utilizing a machine learning algorithm, a reconstructed time series dataset having one or more imputed values for the one or more missing values in the obtained time series dataset, the machine learning algorithm comprising a generative network implementing inverse network parameter determination for network parameters of the generative network;
classifying one or more patterns in the obtained time series dataset utilizing the reconstructed time series dataset;
selecting one or more remedial actions for controlling at least one of the one or more assets based at least in part on the classified one or more patterns in the obtained time series dataset; and
initiating the selected one or more remedial actions to control the at least one asset;
wherein the machine learning algorithm comprises a convolutional neural network; and
wherein generating the reconstructed time series dataset having the one or more imputed values comprises performing two or more iterations of:
applying the obtained time series dataset having the one or more missing values to the convolutional neural network to produce a candidate reconstructed time series dataset having one or more imputed values for the one or more missing values in the obtained time series dataset; and
tuning network parameters of the convolutional neural network using a loss function that compares the candidate reconstructed time series dataset with the obtained time series dataset.

16. The computer program product of claim 15 wherein the convolutional neural network is initialized with randomized values for the network parameters.

17. The computer program product of claim 15 wherein the loss function comprises a regularized loss function comprising a first tunning parameter controlling an amount of regularization induced by a variation loss and a second tuning parameter controlling an amount of regularization induced by regularization of the network parameters of the convolutional neural network, and wherein a value of the first tuning parameter is greater than a value of the second tuning parameter.

18. A method comprising steps of:
obtaining a time series dataset having one or more missing values, the time series dataset comprising monitoring data associated with one or more assets;
generating, utilizing a machine learning algorithm, a reconstructed time series dataset having one or more imputed values for the one or more missing values in the obtained time series dataset, the machine learning algorithm comprising a generative network implementing inverse network parameter determination for network parameters of the generative network;
classifying one or more patterns in the obtained time series dataset utilizing the reconstructed time series dataset;
selecting one or more remedial actions for controlling at least one of the one or more assets based at least in part on the classified one or more patterns in the obtained time series dataset; and
initiating the selected one or more remedial actions to control the at least one asset;
wherein the machine learning algorithm comprises a convolutional neural network;
wherein generating the reconstructed time series dataset having the one or more imputed values comprises performing two or more iterations of:
applying the obtained time series dataset having the one or more missing values to the convolutional neural network to produce a candidate reconstructed time series dataset having one or more imputed values for the one or more missing values in the obtained time series dataset; and
tuning network parameters of the convolutional neural network using a loss function that compares the candidate reconstructed time series dataset with the obtained time series dataset; and wherein the method is performed by at least one processing device comprising a processor coupled to a memory.

19. The method of claim 18 wherein the convolutional neural network is initialized with randomized values for the network parameters.

20. The method of claim 18 wherein the loss function comprises a regularized loss function comprising a first tunning parameter controlling an amount of regularization induced by a variation loss and a second tuning parameter controlling an amount of regularization induced by regularization of the network parameters of the convolutional neural network, and wherein a value of the first tuning parameter is greater than a value of the second tuning parameter.

* * * * *